(12) United States Patent
Shibayama et al.

(10) Patent No.: US 8,460,886 B2
(45) Date of Patent: Jun. 11, 2013

(54) USE OF AN EFFICACY MARKER FOR OPTIMIZING THERAPEUTIC EFFICACY OF AN ANTI-HUMAN PD-1 ANTIBODY ON CANCERS

(75) Inventors: Shiro Shibayama, Ibaraki (JP); Takao Yoshida, Ibaraki (JP); Tamon Hayashi, Ibaraki (JP); Akio Hayashi, Ibaraki (JP); Jun Murai, Ibaraki (JP)

(73) Assignees: Ono Pharmaceutical Co., Ltd., Osaka (JP); Medarex, Inc., Princeton, NJ (US)

( * ) Notice: Subject to any disclaimer, the term of this patent is extended or adjusted under 35 U.S.C. 154(b) by 0 days.

(21) Appl. No.: 13/001,875

(22) PCT Filed: Jul. 3, 2009

(86) PCT No.: PCT/JP2009/003093
§ 371 (c)(1),
(2), (4) Date: Dec. 29, 2010

(87) PCT Pub. No.: WO2010/001617
PCT Pub. Date: Jan. 7, 2010

(65) Prior Publication Data
US 2011/0123550 A1    May 26, 2011

(30) Foreign Application Priority Data
Jul. 4, 2008    (JP) .................................. 2008-176110

(51) Int. Cl.
*G01N 33/53*    (2006.01)
*A61K 39/395*    (2006.01)

(52) U.S. Cl.
USPC ........................................ 435/7.1; 424/130.1

(58) Field of Classification Search
None
See application file for complete search history.

(56) References Cited

U.S. PATENT DOCUMENTS

| 5,629,204 | A | 5/1997 | Honjo et al. |
| 8,008,449 | B2* | 8/2011 | Korman et al. ........... 530/388.15 |
| 2010/0004871 | A1* | 1/2010 | Goldknopf ...................... 702/19 |

FOREIGN PATENT DOCUMENTS

| JP | 7-291996 A | 11/1995 |
| JP | 2006-340714 A | 12/2006 |
| WO | 2006/121168 A1 | 11/2006 |

OTHER PUBLICATIONS

Biancone et al., 1996, J. Exp. Med. 184: 811-819.*
Rantalainen et al., J. Proteome Res., 2006, 5: 2642-2655.*
Berger et al., Clin. Cancer Res., 2008, 14: 3044-3051.*
International Search Report, dated Sep. 1, 2009, issued in Application No. PCT/JP2009/003093, English.
Extended International Search Report dated Jun. 21, 2012, issued by the European Patent Office in counterpart European Application No. 09773195.4.

* cited by examiner

*Primary Examiner* — Ilia Ouspenski
(74) *Attorney, Agent, or Firm* — Sughrue Mion, PLLC

(57) ABSTRACT

A purpose of the present invention is to provide a method capable of more effectively prescribing an anti-human PD-1 antibody for anti-cancer therapy, a method for estimating or optimizing therapeutic efficacy thereof, and further an efficacy marker that can be used in methods thereof. The present invention enables selection of the cancer patient in whom the therapeutic efficacy of the anti-human PD-1 antibody can be expected in future, by measuring the change which is more than a certain level of several kinds of efficacy markers in blood, after administering the initial dose or doses of the anti-human PD-1 antibody compared to that prior to administering the initial dose, and provides a new prescription of the anti-human PD-1 antibody for anti-cancer therapy.

18 Claims, 3 Drawing Sheets

SEQUENCE LISTING

```
<160> NUMBER OF SEQ ID NOS: 14

<210> SEQ ID NO 1
<211> LENGTH: 113
<212> TYPE: PRT
<213> ORGANISM: Homo sapiens

<400> SEQUENCE: 1

Gln Val Gln Leu Val Glu Ser Gly Gly Asp Val Val Gln Pro Gly Gly
1               5                   10                  15

Ser Leu Arg Leu Ser Cys Ala Ala Ser Gly Val Ala Phe Ser Asn Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Met Leu Tyr
65                  70                  75                  80

Leu Gln Met Asn Ser Leu Arg Ala Glu Asp Thr Ala Met Tyr Tyr Cys
                85                  90                  95

Ala Arg Asn Asp Asp Tyr Trp Gly Gln Gly Thr Leu Val Thr Val Ser
            100                 105                 110
```

Ser

<210> SEQ ID NO 2
<211> LENGTH: 113
<212> TYPE: PRT
<213> ORGANISM: Homo sapiens

<400> SEQUENCE: 2

Gln Val Gln Leu Val Glu Ser Gly Gly Asp Val Val Gln Pro Gly Arg
1               5                   10                  15

Ser Leu Arg Leu Ser Cys Ala Ala Ser Gly Leu Thr Phe Thr Asn Tyr
            20                  25                  30

Gly Phe His Trp Val Arg Gln Ala Pro Gly Lys Gly Leu Glu Trp Val
        35                  40                  45

Ala Val Ile Trp Tyr Asp Gly Ser Lys Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Asn Leu Arg Ala Glu Asp Thr Ala Val Tyr Tyr Cys
                85                  90                  95

Ala Thr Gly Asp Asp Tyr Trp Gly Gln Gly Thr Leu Val Thr Val Ser
            100                 105                 110

Ser

<210> SEQ ID NO 3
<211> LENGTH: 113
<212> TYPE: PRT
<213> ORGANISM: Homo sapiens

<400> SEQUENCE: 3

Gln Val Tyr Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Leu Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Thr Ser Leu Arg Val Glu Asp Thr Ala Val Tyr Tyr Cys
                85                  90                  95

Ala Ser Asn Val Asp His Trp Gly Gln Gly Thr Leu Val Thr Val Ser
            100                 105                 110

Ser

<210> SEQ ID NO 4
<211> LENGTH: 113
<212> TYPE: PRT
<213> ORGANISM: Homo sapiens

<400> SEQUENCE: 4

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val

-continued

```
                 35                  40                  45
Ala Val Ile Trp Tyr Asp Gly Ser Lys Arg Tyr Ala Asp Ser Val
 50                  55                  60

Lys Gly Arg Phe Thr Ile Ser Arg Asp Asn Ser Lys Asn Thr Leu Phe
 65                  70                  75                  80

Leu Gln Met Asn Ser Leu Arg Ala Glu Asp Thr Ala Val Tyr Tyr Cys
                 85                  90                  95

Ala Thr Asn Asp Asp Tyr Trp Gly Gln Gly Thr Leu Val Thr Val Ser
                100                 105                 110

Ser

<210> SEQ ID NO 5
<211> LENGTH: 121
<212> TYPE: PRT
<213> ORGANISM: Homo sapiens

<400> SEQUENCE: 5

Gln Leu Gln Leu Gln Glu Ser Gly Pro Gly Leu Val Lys Pro Ser Glu
 1               5                  10                  15

Thr Leu Ser Leu Thr Cys Thr Val Ser Gly Gly Ser Leu Ser Arg Ser
                 20                  25                  30

Ser Phe Phe Trp Gly Trp Ile Arg Gln Pro Pro Gly Lys Gly Leu Glu
                 35                  40                  45

Trp Ile Gly Ser Ile Tyr Tyr Ser Gly Ser Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Val Arg Asp Tyr Asp Ile Leu Thr Gly Asp Glu Asp Tyr Trp Gly
                100                 105                 110

Gln Gly Thr Leu Val Thr Val Ser Ser
                115                 120

<210> SEQ ID NO 6
<211> LENGTH: 113
<212> TYPE: PRT
<213> ORGANISM: Homo sapiens

<400> SEQUENCE: 6

Gln Val Gln Leu Val Glu Ser Gly Gly Gly Val Val Gln Pro Gly Arg
 1               5                  10                  15

Ser Leu Arg Leu Ser Cys Thr Thr Ser Gly Ile Thr Phe Ser Ser Tyr
                 20                  25                  30

Gly Phe His Trp Val Arg Gln Ala Pro Gly Lys Gly Leu Glu Trp Val
                 35                  40                  45

Ala Val Ile Trp Tyr Asp Gly Ser Lys Lys Tyr Ala Asp Ser Val
 50                  55                  60

Lys Gly Arg Phe Thr Leu Ser Arg Asp Asp Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Val Thr Gly Asp Asp Tyr Trp Gly Gln Gly Thr Leu Val Thr Val Ser
                100                 105                 110

Ser
```

-continued

<210> SEQ ID NO 7
<211> LENGTH: 121
<212> TYPE: PRT
<213> ORGANISM: Homo sapiens

<400> SEQUENCE: 7

Gln Leu Gln Leu Gln Glu Ser Gly Pro Gly Leu Val Lys Pro Ser Glu
1               5                   10                  15

Thr Leu Ser Leu Thr Cys Ser Val Ser Gly Gly Ser Leu Ser Arg Ser
            20                  25                  30

Ser Tyr Phe Trp Gly Trp Ile Arg Gln Pro Pro Gly Lys Gly Leu Glu
        35                  40                  45

Trp Ile Ala Ser Ile Phe Tyr Ser Gly Glu Thr Tyr Phe Asn Pro Ser
    50                  55                  60

Leu Lys Ser Arg Val Thr Ile Ser Val Asp Thr Ser Arg Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Tyr Asp Ile Leu Thr Gly Asp Glu Asp Tyr Trp Gly
            100                 105                 110

Gln Gly Thr Leu Val Thr Val Ser Ser
        115                 120

<210> SEQ ID NO 8
<211> LENGTH: 107
<212> TYPE: PRT
<213> ORGANISM: Homo sapiens

<400> SEQUENCE: 8

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Ile Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
            100                 105

<210> SEQ ID NO 9
<211> LENGTH: 107
<212> TYPE: PRT
<213> ORGANISM: Homo sapiens

<400> SEQUENCE: 9

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Thr Ser Asn Arg Ala Thr Gly Ile Pro Ala Arg Phe Ser Gly
    50                  55                  60

```
Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Leu
                 85                  90                  95

Thr Phe Gly Gly Gly Thr Lys Val Glu Ile Lys
                100                 105

<210> SEQ ID NO 10
<211> LENGTH: 107
<212> TYPE: PRT
<213> ORGANISM: Homo sapiens

<400> SEQUENCE: 10

Glu Ile Val Leu Thr Gln Ser Pro Ala Thr Leu Ser Leu Ser Pro Gly
  1               5                  10                  15

Glu Arg Ala Thr Leu Ser Cys Arg Ala Ser Gln Ser Val Ser Ser Tyr
                 20                  25                  30

Leu Ala Trp Tyr Gln Gln Lys Pro Gly Gln Ala Pro Arg Leu Leu Ile
             35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Ser Ser Asn Trp Pro Arg
                 85                  90                  95

Thr Phe Gly Gln Gly Thr Lys Val Glu Ile Lys
                100                 105

<210> SEQ ID NO 11
<211> LENGTH: 107
<212> TYPE: PRT
<213> ORGANISM: Homo sapiens

<400> SEQUENCE: 11

Glu Ile Val Leu Thr Gln Ser Pro Ala Thr Leu Ser Leu Ser Pro Gly
  1               5                  10                  15

Glu Arg Ala Thr Leu Ser Cys Arg Ala Ser Gln Ser Val Ser Ser Tyr
                 20                  25                  30

Leu Ala Trp Tyr Gln Gln Lys Pro Gly Gln Ala Pro Arg Leu Leu Ile
             35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Ser Ser Asn Trp Pro Arg
                 85                  90                  95

Thr Phe Gly Gln Gly Thr Lys Val Glu Ile Lys
                100                 105

<210> SEQ ID NO 12
<211> LENGTH: 107
<212> TYPE: PRT
<213> ORGANISM: Homo sapiens

<400> SEQUENCE: 12

Asp Ile Gln Met Thr Gln Ser Pro Ser Ser Leu Ser Ala Ser Val Gly
  1               5                  10                  15

Asp Arg Val Ser Ile Thr Cys Arg Ala Ser Gln Gly Ile Ser Ser Trp
                 20                  25                  30
```

Leu Ala Trp Tyr Gln Gln Lys Pro Glu Lys Ala Pro Lys Ser Leu Ile
            35                  40                  45

Tyr Ala Ala Ser Asn Leu Arg Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Tyr Ser Tyr Pro Arg
                 85                  90                  95

Thr Phe Gly Gln Gly Thr Lys Val Glu Ile Lys
            100                 105

<210> SEQ ID NO 13
<211> LENGTH: 107
<212> TYPE: PRT
<213> ORGANISM: Homo sapiens

<400> SEQUENCE: 13

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
                 20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Leu
                 85                  90                  95

Thr Phe Gly Gly Gly Thr Lys Val Glu Ile Lys
            100                 105

<210> SEQ ID NO 14
<211> LENGTH: 107
<212> TYPE: PRT
<213> ORGANISM: Homo sapiens

<400> SEQUENCE: 14

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Trp
                 20                  25                  30

Leu Ala Trp Tyr Gln Gln Lys Pro Glu Lys Ala Pro Lys Ser Leu Ile
            35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Tyr Ser Tyr Pro Arg
                 85                  90                  95

Thr Phe Gly Gln Gly Thr Lys Val Glu Ile Lys
            100                 105

USE OF AN EFFICACY MARKER FOR OPTIMIZING THERAPEUTIC EFFICACY OF AN ANTI-HUMAN PD-1 ANTIBODY ON CANCERS

TECHNICAL FIELD

The present invention relates to use of an efficacy marker for estimating or optimizing therapeutic efficacy of an anti-human PD-1 antibody for a particular cancer patient.

BACKGROUND ART

Currently, the first standard therapy for the permanent cure for cancer is chemical therapy, hormone therapy, or irradiation therapy, or combination thereof, but there has been a problem of occurrence of the side-effects. On the other hand, immune therapy has attracted attention as a promising therapy that avoids the side effects of traditional therapies. However, a characteristic of the immune therapy is mechanisms of action via cancer immunity of a patient, and therefore a large part of the therapy is yet unclear, its effects are different among individuals, and it is said that a relatively long term is required for treatment. In particular, in the case of a new medical agent that may require a relatively long period of treatment, it is very difficult to determine timing for evaluation of effectiveness for each of the patients, and in the case of adopting conventional timing to evaluate, even if the therapy can actually generate anti-tumor effects, its evaluation would be determined as no effect before confirming the effect. Therefore, in order to overcome the problem for the immune therapy, a method for detecting a pharmacological reaction before the timing to judge the effect, namely, a determination method capable of estimating the treatment effect has been required.

The anti-human PD-1 antibody is utilized as an anticancer and as an agent for fighting infectious diseases. It acts as an agent for enhancing cancer immunity by suppressing the immune suppression signal via PD-1, which is an immune suppression receptor (See US 2009/0217401, WO 03/011911, and WO 04/004771, incorporated herein by reference in their entirety.). However, a determination method capable of estimating the therapeutic effects has not been reported yet.

The present invention provides compositions and methods for detecting the efficacy of anti-human PD-1 antibody therapies and includes immunoglobulin(s), CD5L, gelsolin, and the like, which change in the blood, as biomarkers capable of estimating the therapeutic effects by the anti-human PD-1 antibody. For the immunoglobulins, in Nishimura et al., (and three persons), International Immunology, Vol. 10, No. 10, 1998, p. 1563-1572, it has been reported that the increase of serum $IgG_3$, $IgG_{2b}$, and IgA of the PD-1 deficient mouse is observed, and for gelsolin, in Yang et al., (and nine persons), BMC Cancer, Vol. 6, No. 203, 2006, p. 1-10, the relationship between expression amount of gelsolin and death risk has been reported, but the relationship between the gelsolin expression level and the anti-cancer effects by the anti-human PD-1 antibody has not been reported at all.

SUMMARY OF INVENTION

A purpose of the present invention is to provide a method for more effectively prescribing an anti-human PD-1 antibody for a particular cancer patient, a method for estimating or optimizing therapeutic efficacy thereof, and further the efficacy marker that can be used in methods thereof.

The present invention provides efficacy markers in blood that change prior to the therapeutic effects of an anti-human PD-1 antibody.

In preferred embodiments, the present invention provides.

[1] A method for optimizing therapeutic efficacy of an anti-human PD-1 antibody on cancer, comprising subsequently administering one or more doses of an anti-human PD-1 antibody in the cancer patient in whom concentrations of one or more efficacy markers in blood after administering an initial dose or doses of the anti-human PD-1 antibody significantly increased more than those prior to administering the initial dose, wherein one or more efficacy markers is/are selected from the group consisting of immunoglobulin(s), CD5L, gelsolin, and fragments thereof.

[2] The method of [1], wherein the concentrations of the efficacy markers in blood after administering an initial dose or doses of the anti-human PD-1 antibody are those at any timing before the twelfth week after administering the initial dose.

[3] The method of [1], wherein the concentrations of the efficacy markers in blood after administering an initial dose or doses of the anti-human PD-1 antibody are those at any timing before the eighth week after administering the initial dose.

[4] The method of [1], wherein the immunoglobulin(s) is/are one or more isotypes selected from the group consisting of IgM, IgG and IgA.

[5] The method of [4], wherein IgG is $IgG_4$.

[6] The method of [1], wherein the anti-human PD-1 antibody is a human anti-human PD-1 antibody.

[7] The method of [6], wherein the human anti-human PD-1 antibody is the antibody specified as 17D8, 4H1, 5C4, 4A11, 7D3, 5F4, or 2D3 described in US 2009/0217401.

[8] The method of [1], wherein the cancer patient is a patient having one or more kinds of solid cancers.

[9] The method of [8], wherein one or more kinds of solid cancers is/are selected from the group consisting of malignant melanoma, kidney cancer, prostate cancer, breast cancer, lung cancer, pancreatic cancer, intestinal cancer, liver cell cancer, biliary tract cancer, stomach cancer, ovary cancer, esophageal cancer, and urothelial cancer.

[10] Use of one or more efficacy markers for optimizing therapeutic efficacy of an anti-human PD-1 antibody on cancer, wherein the optimization comprises subsequently administering one or more doses of the anti-human PD-1 antibody in the cancer patient in whom concentrations of one or more efficacy markers in blood after administering an initial dose or doses of the anti-human PD-1 antibody significantly increased more than those prior to administering the initial dose, wherein one or more efficacy markers is/are selected from the group consisting of immunoglobulin(s), CD5L, gelsolin, and fragments thereof.

[11] The use of [10], wherein the concentrations of the efficacy markers in blood after administering an initial dose or doses of the anti-human PD-1 antibody are those at any timing before the twelfth week after administering the initial dose.

[12] The use of [10], wherein the concentrations of the efficacy markers in blood after administering an initial dose or doses of the anti-human PD-1 antibody are those at any timing before the eighth week after administering the initial dose.

[13] The use of [10], wherein the immunoglobulin(s) is/are one or more isotypes selected from the group consisting of IgM, IgG and IgA.

[14] The use of [13], wherein IgG is $IgG_4$.

[15] The use of [10], wherein the anti-human PD-1 antibody is a human anti-human PD-1 antibody.

[16] The use of [15], wherein the human anti-human PD-1 antibody is the antibody specified as 17D8, 4H1, 5C4, 4A11, 7D3, 5F4, or 2D3 described in US 2009/0217401.

[17] The use of [10], wherein the cancer patient is a patient having one or more kinds of solid cancers.

[18] The use of [17], wherein one or more kinds of solid cancers is/are selected from the group consisting of malignant melanoma, kidney cancer, prostate cancer, breast cancer, lung cancer, pancreatic cancer, intestinal cancer, liver cell cancer, biliary tract cancer, stomach cancer, ovary cancer, esophageal cancer and urothelial cancer.

[19] A method of treating for cancer, comprising subsequently administering one or more doses of an anti-human PD-1 antibody in the cancer patient in whom concentrations of one or more efficacy markers in blood after administering an initial dose or doses of the anti-human PD-1 antibody significantly increased more than those prior to administering the initial dose, wherein one or more efficacy markers is/are selected from the group consisting of immunoglobulin(s), CD5L, gelsolin, and fragments thereof.

[20] The method of [19], wherein the concentrations of the efficacy markers in blood after administering an initial dose or doses of the anti-human PD-1 antibody are those at any timing before the twelfth week after administering the initial dose.

[21] The method of [19], wherein the concentrations of the efficacy markers in blood after administering an initial dose or doses of the anti-human PD-1 antibody are those at any timing before the eighth week after administering the initial dose.

[22] The method of [19], wherein the immunoglobulin(s) is/are one or more isotypes selected from the group consisting of IgM, IgG and IgA.

[23] The method of [22], wherein IgG is $IgG_4$.

[24] The method of [19], wherein the anti-human PD-1 antibody is a human anti-human PD-1 antibody.

[25] The method of [24], wherein the human anti-human PD-1 antibody is the antibody specified as 17D8, 4H1, 5C4, 4A11, 7D3, 5F4, or 2D3 described in US 2009/0217401.

[26] The method of [19], wherein the cancer patient is a patient having one or more kinds of solid cancers.

[27] The method of [26], wherein one or more kinds of solid cancers is/are selected from the group consisting of malignant melanoma, kidney cancer, prostate cancer, breast cancer, lung cancer, pancreatic cancer, intestinal cancer, liver cell cancer, biliary tract cancer, stomach cancer, ovary cancer, esophageal cancer, and urothelial cancer.

[28] An anticancer agent comprising an anti-human PD-1 antibody for treating the cancer patient in whom concentrations of one or more efficacy markers in blood after administering an initial dose or doses of the anti-human PD-1 antibody significantly increased more than those prior to administering the initial dose, wherein one or more efficacy markers is/are selected from the group consisting of immunoglobulin(s), CD5L, gelsolin, and fragments thereof.

[29] The anticancer agent of [28], wherein the concentrations of the efficacy markers in blood after administering an initial dose or doses of the anti-human PD-1 antibody are those at any timing before the twelfth week after administering the initial dose.

[30] The anticancer agent of [28], wherein the concentrations of the efficacy markers in blood after administering an initial dose or doses of the anti-human PD-1 antibody are those at any timing before the eighth week after administering the initial dose.

[31] The anticancer agent of [28], wherein the immunoglobulin(s) is/are one or more isotypes selected from the group consisting of IgM, IgG and IgA.

[32] The anticancer agent of [31], wherein IgG is $IgG_4$.

[33] The anticancer agent of [28], wherein the anti-human PD-1 antibody is a human anti-human PD-1 antibody.

[34] The anticancer agent of [33], wherein the human anti-human PD-1 antibody is the antibody specified as 17D8, 4H1, 5C4, 4A11, 7D3, 5F4 or 2D3 described in US 2009/0217401.

[35] The anticancer agent of [28], wherein the cancer patient is a patient having one or more kinds of solid cancers.

[36] The anticancer agent of [35], wherein one or more kinds of solid cancers is/are selected from the group consisting of malignant melanoma, kidney cancer, prostate cancer, breast cancer, lung cancer, pancreatic cancer, intestinal cancer, liver cell cancer, biliary tract cancer, stomach cancer, ovary cancer, esophageal cancer and urothelial cancer.

[37] A method for estimating therapeutic efficacy of an anti-human PD-1 antibody on cancer, comprising comparing the concentrations of one or more efficacy markers in cancer patient's blood after administering an initial dose or doses of the anti-human PD-1 antibody with those prior to administering the initial dose and estimating that the anti-human PD-1 antibody is effective on treatment for cancers, based on significant increase of the concentrations of one or more efficacy markers after administering an initial dose or doses compared to those prior to administering the initial dose, wherein one or more efficacy markers is/are selected from immunoglobulin(s), CD5L, gelsolin and fragments thereof.

[38] The method of [37], wherein the therapeutic efficacy is estimated based on significant increase of the concentrations of one or more efficacy markers in blood at any timing before the twelfth week after administering the initial dose compared to those prior to administering the initial dose.

[39] The method of [37], wherein the therapeutic efficacy is estimated based on significant increase of the concentrations of one or more efficacy markers in blood at any timing before the eighth week after administering the initial dose compared to those prior to administering the initial dose.

[40] The method of [37], wherein the immunoglobulin(s) is/are one or more isotypes selected from the group consisting of IgM, IgG and IgA.

[41] The method of [40], wherein IgG is $IgG_4$.

[42] The method of [37], wherein the cancer patient is a patient having one or more kinds of solid cancers.

[43] The method of [42], wherein the solid cancer(s) is/are one or more kinds selected from the group consisting of malignant melanoma, kidney cancer, prostate cancer, breast cancer, lung cancer, pancreatic cancer, intestinal cancer, liver cell cancer, biliary tract cancer, stomach cancer, ovary cancer, esophageal cancer and urothelial cancer.

[44] The method of [37], wherein the anti-human PD-1 antibody is a human anti-human PD-1 antibody.

[45] The method of [44], wherein the anti-human PD-1 antibody is the human antibody specified as 17D8, 4H1, 5C4, 4A11, 7D3, 5F4 or 2D3 described in US 2009/0217401.

[46] A method for selecting the patient suitable for the treatment for cancer with an anti-human PD-1 antibody, comprising selecting the patient in whom concentrations of one or more efficacy markers in blood after administering an initial dose or doses of an anti-human PD-1 antibody significantly increased more than those prior to administering the initial dose, wherein one or more efficacy markers is/are selected from the group consisting of immunoglobulin(s), CD5L, gelsolin, and fragments thereof.

The present invention provides a new prescription method of the anti-human PD-1 antibody for anti-cancer therapy that is proceeded to administer to the cancer patient in whom its effect can be expected in future and that is not administered or is early stopped being administered to a patient in whom its effect can't be expected.

BEST MODE FOR CARRYING OUT THE INVENTION

Figure 1:
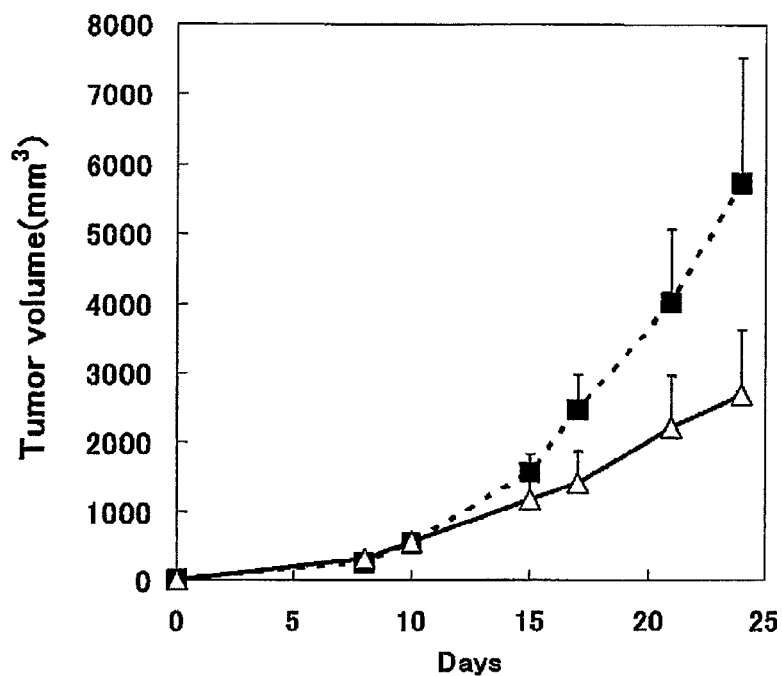
FIG. 1 shows an effect of administration of the anti-mPD-1 antibody 4H2 on tumor volume.

Hereinafter, the present invention will be explained in detail.

In the present invention, human PD-1 is a protein specified by JP 07-291996.

In the present invention, the anti-human PD-1 antibody is, for example, a humanized anti-human PD-1 antibody or a human anti-human PD-1 antibody that is so-called a human PD-1 antagonist antibody or a human PD-1 neutralizing antibody capable of inhibiting immune suppression signal of human PD-1 wherein the humanized anti-human PD-1 antibody represents the antibody in which CDR (Complementarity Determining Region) sequence of an anti-human PD-1 antibody derived from another mammal such as a mouse is transplanted onto a framework sequence of a human antibody, and includes antibodies described in, for example, WO 06/021955.

Moreover, the human anti-human PD-1 antibody is the anti-human PD-1 antibody of which all of the structures such as CDR and the framework are derived from human, and includes antibodies described in, for example, WO 04/056875 and US 2009/0217401, preferably is a human anti-human PD-1 antibody specified as 17D8 (having $V_H$ and $V_L$ sequences as shown in SEQ ID NOs: 1 and 8, respectively), 4H1 (having $V_H$ and $V_L$ sequences as shown in SEQ ID NOs: 3 and 10, respectively), 5C4 (having $V_H$ and $V_L$ sequences as shown in SEQ ID NOs: 4 and 11, respectively), 4A11 (having $V_H$ and $V_L$ sequences as shown in SEQ ID NOs: 5 and 12, respectively), 7D3 (having $V_H$ and $V_L$ sequences as shown in SEQ ID NOs: 6 and 13, respectively), 5F4 (having $V_H$ and $V_L$ sequences as shown in SEQ ID NOs: 7 and 14, respectively) or 2D3 (having $V_H$ and $V_L$ sequences as shown in SEQ ID NOs: 2 and 9, respectively) described in US 2009/0217401.

The above anti-human PD-1 antibodies can be produced based on methods described in the respective disclosed publications. Moreover, in the present invention, the anti-human PD-1 antibody includes an antibody fragment such as Fab, F(ab)'$_2$, ScFv of the above antibodies, and a low-molecular antibody such as Sc(Fv)$_2$ or diabody.

In the present invention, as an efficacy marker, namely, a marker capable of evaluating the therapeutic efficacy of the anti-human PD-1 antibody on cancer is a biological molecule or a fragment thereof of which the significant concentration change in cancer patient's blood prior to administering the initial dose and after administering the initial dose or doses of the anti-human PD-1 antibody in the cancer patient can be detected. For example, molecules of which the concentration increases include any one or more molecules selected from the group consisting of immunoglobulin(s), CD5L (CD5-like), gelsolin, complement C3, apolipoprotein, hemoglobin beta chain, mannose binding lectin, serpin A6, homeobox A10, EDEL3 (EGF-like repeats and discoidin I-like domains-containing protein 3), fibronectin 1, inter-alpha trypsin inhibitor 1, complement C4-B, C4b-binding protein, Ig kappa chain VIII region, immunoglobulin gamma 1 chain C region, angiotensinogen, alpha-1-antitrypsin-1, albumin, clotting factor XIII, kindlin 3, prothrombin, serine protease inhibitor A3K, Alpha-1 macroglobulin, plasminogen, complement B factor, murinoglobulin-1, murinoglobulin-4, integrin alpha 5 and fragments thereof, and are preferably any one or more molecules selected from the group consisting of the immunoglobulin(s), CD5L, gelsolin and fragments thereof, more preferably any one or more molecules selected from the group consisting of the immunoglobulin(s), CD5L and fragments thereof, and further preferably the immunoglobulin(s) or fragment(s) thereof. On the other hand, molecules of which the concentration decreases include any one or more molecules selected from the group consisting of haptoglobin, serum amyloid P component, serum amyloid A1, serum amyloid A2, serotransferrin, complement component factor H, Complement C9, Inter-alpha trypsin inhibitor, hemopexin, thrombospondin-1 and fragments thereof. Here, the fragment of the molecule means one part of the biological molecule degraded by pretreatment for the measurement (for example, degradation by digestive enzyme such as trypsin) or by serum enzyme or the like.

In the present invention, the immunoglobulins include all of isotypes of, for example, IgM, IgG (such as $IgG_1$, $IgG_2$, $IgG_3$ or $IgG_4$), IgA (such as $IgA_1$ or $IgA_2$), IgD and IgE, preferably IgM, IgA or IgG, more preferably IgM or $IgG_4$. Moreover, the immunoglobulin concentration in blood means concentration of each isotype.

In the present invention, the respective efficacy marker is a protein specified by GenBank accession numbers in the following tables 1 to 3. In the tables, when there are many of accession numbers for one marker, it is indicated that the marker is specified by any one of the numbers. Moreover, the marker to which the sign "*" is appended is specified by the mentioned accession number as a mouse protein, and the marker to which the sign "**" is appended is specified by the mentioned accession number as a rat protein.

TABLE 1

| Markers | GenBank Acc. Num. |
| --- | --- |
| CD5L | NP_005885.1 |
| Gelsolin | NP_000168.1 |
| C3 complement | NP_000055.2 |
| Apolipoprotein | NP_000030.1 |
| Hemoglobin beta chain | NP_000509.1 |
| Mannose-binding lectin | NP_000233.1 |
| Serpin A6 | NP_001747.2 |

TABLE 2

| Markers | GenBank Acc. Num. |
| --- | --- |
| Homeobox A10 | NP_061824.3 |
|  | NP_714926.1 |
| EDEL3 | NP_005702.3 |
| fibronectin 1 | NP_002017.1 |
|  | NP_473375.2 |
|  | NP_997639.1 |
|  | NP_997640.1 |
|  | NP_997641.1 |
|  | NP_997643.1 |
|  | NP_997647.1 |
| Inter-alpha-trypsin inhibitor 1 | NP_002206.2 |
| C4B complement | NP_001002029.3 |
| C4B complement binding protein | NP_000706.1 |
|  | NP_000707.1 |
|  | NP_001017364.1 |
|  | NP_001017365.1 |
|  | NP_001017366.1 |
|  | NP_001017367.1 |
| Immunoglobulin kappa chain VIII region | S16833 |
|  | S40381 |
| Immunoglobulin gamma 1 chain C region | NP_064455.1 |
|  | NP_690594.1 |
| Angiotensinogen | NP_000020.1 |
| Apha 1 antitrypsin 1 | NP_000286.3 |
|  | NP_001002235.1 |
|  | NP_001002236.1 |
|  | NP_001121172.1 |
|  | NP_001121173.1 |
|  | NP_001121174.1 |
|  | NP_001121175. |
|  | NP_001121176.1 |
|  | NP_001121177.1 |
|  | NP_001121178.1 |
|  | NP_001121179.1 |
| Albumin | NP_000468.1 |
| Coagulation factor XIII | NP_001985 |
| KINDLIN3 | NP_113659.3 |
|  | NP_848537.1 |
| SPA3K* | NP_035588.1 |
| Prothrombin | NP_000497.1 |
| Alpha-1 Macroglobulin | NP_001624.1 |
| Plasminogen | NP_000292.1 |
| Complement factor B | NP_001701.2 |
| Murinoglobulin-1* | NP_032671.2 |
| Murinoglobulin-4** | XR_035729.1 |
| Integrin alpha 5 | NP_002196.2 |

TABLE 3

| Markers | GenBank Acc. Num. |
| --- | --- |
| Haptoglobin | NP_001119574.1 |
|  | NP_005134.1 |
| Amyloid P Component | NP_001630.1 |
| Serum Amyloid A1 | NP_000322.2 |
|  | NP_954630.1 |
| Serum Amyloid A2 | NP_001120852.1 |
|  | NP_110381.2 |
| Serotransferrin | NP_001054.1 |
| Complement factor H | NP_000177.2 |
|  | NP_001014975.1 |
| C9 complement | NP_001728.1 |
| Inter-alpha-trypsin inhibitor | NP_002208.3 |
| Hemopexin | NP_000604.1 |
| Thrombospondin-1 | NP_003237.2 |

In the present invention, the timing prior to the administration of the anti-human PD-1 antibody can be any timing prior to administering the initial dose, but the timing immediately prior to administering the initial dose is preferable. On the other hand, the timing after administering the initial dose or doses of the anti-human PD-1 antibody can be any timing prior to confirming the anticancer effects of the anti-human PD-1 antibody by conventional measurement or a conventional evaluation method, but is more preferably any timing prior to approximately the twelfth week (more preferably, the eighth week) after administering the initial dose of the anti-human PD-1 antibody, further preferably the earliest timing in which a certain or more amount of change in the efficacy marker concentration in blood after the administration is observed and which is prior to approximately the eighth week after administering the initial dose. Moreover, the blood sampling and the measurement of the efficacy marker concentration after administering the initial dose or doses are not limited to one time, but are preferably performed at a plurality of times (for example, two to twelve times or more).

A dosage of the anti-human PD-1 antibody varies depending on age, weight, symptom (such as cancer), treatment effect, administration method, treatment time and the like, but the administration is performed, for example, in the range of about 1 to 30 mg/kg at one time, at one time every two to four weeks, for twelve weeks (at 3 to 6 times). Of course, as described above, the dosage varies depending on various conditions, and therefore a less dosage than the above range may be sufficient, or the dosage over the above range may be required to be administered.

For the patient in whom significant change in the efficacy marker concentration in blood is not observed by the administration of the anti-human PD-1 antibody, until at least the significant change can be observed, a modified prescription such as increase in the dosage in the range of about 1 to 30 mg/kg, extension of dosing period, increase in the number of doses, or shortening of the dosing intervals may be performed.

In the present invention, the therapeutic efficacy on cancer may be evaluated based on Response Evaluation Criteria In Solid Tumors (hereinafter, abbreviated as RECIST) (Journal of the National Cancer Institute, 2000, Vol. 92, No. 3, 205-216), namely Complete Response (hereinafter abbreviated to CR) in which disappearance of all target lesions continues for four weeks or more, Partial Response (hereinafter abbreviated to PR) in which 30% or more decrease in the sum of the longest diameters of target lesions continues for four weeks or more, Progressive Disease (hereinafter abbreviated to PD) in which the sum of the longest diameters of target lesions increases by 20% or more, compared with the smallest sum of the longest diameters recorded after the initiation of the treatment, and Stable Disease (hereinafter abbreviated as SD) in which shrinkage of tumor is insufficient for PR and increase of tumor, compared with the smallest sum of the longest diameters after the initiation of the treatment is insufficient for PD.

In the present invention, the significant increase of concentration of the efficacy marker in cancer patient's blood after administering the initial dose or doses of the anti-human PD-1 antibody over that prior to administering the initial dose means that the concentration of the efficacy marker after administering the initial dose or doses is more than the lower point of blood concentration range of the efficacy marker in the patient group evaluated as SD in RECIST, and may also mean that increase of blood concentration after administering the initial dose or doses over that prior to administering the initial dose is more than the lower point of range of said increase in the SD patient group. Further, when at least one kind of many efficacy markers meets the requirement above, said increase can be significant. And, blood concentration range of or said increase in each efficacy marker in each classification (CR, PR, SD, PD), particularly SD, can be calculated by statistical analysis of blood concentration or said increase in blood concentration over that prior to administering the initial dose in the patients evaluated as SD from many of cancer patients in which the anti-human PD-1 antibody is administered in advance.

The present invention includes the method for estimating the therapeutic efficacy of the anti-human PD-1 antibody on cancers comprising;
(1) measuring concentrations of one or more efficacy markers above in cancer patient's blood prior to administering the initial dose of the anti-human PD-1 antibody and those after administering the initial dose or doses, respectively;
(2) comparing both concentrations of one or more efficacy markers; and
(3) estimating that the anti-human PD-1 antibody is effective on treatment for cancers, based on the significant increase of the concentrations of one or more efficacy markers after administering the initial dose or doses compared to those prior to administering the initial dose.

Further, the present invention includes the method for optimizing the therapeutic efficacy of the anti-human PD-1 antibody on cancers, comprising:
(1) measuring concentrations of one or more efficacy markers above in cancer patient's blood prior to administering the initial dose of the anti-human PD-1 antibody and those after administering the initial dose or doses, respectively;
(2) comparing both concentrations of one or more efficacy markers; and
(3) subsequently administering one or more doses of the anti-human PD-1 antibody in the cancer patient in whom the concentrations of one or more efficacy markers in blood after administering the initial dose or doses of the anti-human PD-1 antibody significantly increased more than those prior to administering the initial dose.

Likewise, the present invention includes the use of one or more efficacy markers above for optimization of the therapeutic efficacy of an anti-human PD-1 antibody on cancers, wherein the optimization comprises;
(1) measuring concentrations of one or more efficacy markers above in cancer patient's blood prior to administering the initial dose of the anti-human PD-1 antibody and those after administering the initial dose or doses, respectively
(2) comparing both concentrations of one or more efficacy markers; and
(3) subsequently administering one or more doses of the anti-human PD-1 antibody in the cancer patient in whom the concentrations of one or more efficacy markers in blood after administering the initial dose or doses of the anti-human PD-1 antibody significantly increased more than those prior to administering the initial dose.

Further, the present invention includes the method of treating for cancer, comprising subsequently administering one or more doses of an anti-human PD-1 antibody in the cancer patient in whom concentrations of one or more efficacy markers above in blood after administering the initial dose or doses of the anti-human PD-1 antibody significantly increase more than those prior to administering the initial dose.

For measurement of concentrations of the efficacy markers, each cancer patient's blood before and after the administration of the anti-human PD-1 antibody is used. The method of blood sampling is not particularly limited, but to prevent blood clotting, an anticoagulant agent may be used. The anticoagulant agent includes heparin, sodium citrate, EDTA and the like. The blood may be separated into serum by a well-known method in the art or the method described in Examples and may be measured as it is or may be stored. When blood concentrations of many efficacy markers are measured, each efficacy marker may be measured individually, or all thereof may be measured cyclopaedically.

In the present invention, concentrations of the efficacy markers, particularly the immunoglobulin(s), CD5L, gelsolin or fragments thereof can be measured by a well-known method in the art, preferably an immunological method and a mass spectrometric method.

The immunological measurement can be conducted by a well-known method in the art or the method described in Examples, and includes, for example, enzyme immunoassay (EIA) (such as enzyme-linked immunosorbent assay (ELISA), chemiluminescent immunoassay (CLIA) and electrochemiluminescence immunoassay (ECLIA)), radioimmune assay (RIA) (such as immuno radio metric assay (IRMA), radio receptor assay (RRA), radio assay (RA) and competitive protein binding assay (CPBA)), fluorescence antibody technique (FA) (such as fluoroimmunoassay (FIA), time-resolvedifluoroimmunoassay (TR-FAI), indirect fluorescent antibody technique (IFA)), fluorescence polarization immunoassay (FPIA) (such as Evanescent wave fluoroimmunoassay (EV-FIA) and Fluorescence polarization assay (FPA)), immunoprecipitation technique, turbidimetrical immunoassay (TIA), particle counting immunoassay (PCIA) (such as latex agglutination (LA), particle mediated immunoassay (PAM-IA) and latex photometric immunoassay (LPIA)), nephelometry method, western blotting, immunostaining, immunodiffusion method and the like.

The mass spectrometric method can be conducted by a well-known method in the art, for example, supplying samples to the method of combining a sample-introducing part (such as gel electrophoresis pathway, liquid chromatography (such as ion-exchange chromatography, hydrophobic chromatography, affinity chromatography, and reverse phase chromatography)), a ion source (such as electron ionization, chemical ionization, field desorption, high-speed atomic collision, matrix-assisted laser desorption/ionization, electrospray ionization, and atmospherical pressure chemical ionization) and a mass spectrometer (double-focusing mass spectrometer, quadrupole mass spectrometer, time-of-flight mass spectrometer, and Fourier transform mass spectrometer, ion cyclotron mass spectrometer), and detecting bands, spots or peaks corresponding to the molecular mass of predefined marker peptides, and specifically includes liquid chromatography-mass spectrometry (LC-MS) or liquid chromatography-tandem mass spectrometry (LC-MS/MS).

In the present invention, in particular, when the efficacy marker is the immunoglobulin or fragments thereof, the measurement is preferably ELISA, turbidimetrical immunoassay, nephelometry or latex photometric immunoassay, and when the efficacy marker is CD5L or gelsolin or fragments thereof, the measurement is preferably ELISA or the mass spectrometric method (such as LC/MS or LC/MS/MS).

The cancer patient to whom the present invention can be applied is not particularly limited, but its effect can be more expected in the patient having solid cancer. Such solid cancer includes, for example, malignant melanoma (melanoma (such as metastatic malignant melanoma)), kidney cancer (such as renal cell cancer, and clear cell carcinoma), prostate cancer (such as hormone refractory prostate adenocarcinoma), breast cancer, lung cancer (such as non-small-cell lung cancer), pancreatic cancer, intestinal cancer, liver cell cancer, biliary tract cancer, stomach cancer, ovary cancer, esophageal cancer, urothelial cancer, colonic cancer, bone cancer, skin cancer, head and neck cancer, skin or orbital malignant melanoma, uterus cancer, rectal cancer, anal cancer, testicle cancer, tubal carcinoma, endometrial carcinoma, uterus neck carcinoma, vaginal carcinoma, vulva carcinoma, small intestinal cancer, endocrine system cancer, thyroid cancer, parathyroid cancer, adrenal cancer, soft tissue sarcomas, urethral cancer, penis cancer, childhood solid cancer, bladder cancer, renal or ureter cancer, renal pelvic carcinoma, central nervous system (CNS) tumor, tumor new vascular channel formation, spine tumor, brain-stem glioma, pituitary adenoma, Kaposi's sarcoma, squamous cell cancer, carcinoma planocellulare and environment-induced cancer including asbestos-induced cancer and combinations of the cancers. The solid cancer for which the effect of the present invention can be more expected includes malignant melanoma (melanoma (such as metastatic malignant melanoma)), kidney cancer (such as renal cell cancer and clear cell carcinoma), prostate cancer (such as hormone refractory prostate adenocarcinoma), breast cancer, lung cancer (such as non-small-cell lung cancer), pancreatic cancer, intestinal cancer, liver cell cancer, biliary tract cancer, stomach cancer, ovary cancer, esophageal cancer, urothelial cancer and combination of the cancers. The solid cancer for which further effect of the present invention can be expected includes malignant melanoma (melanoma (such as metastatic malignant melanoma)), kidney cancer (such as renal cell cancer and clear cell carcinoma), prostate cancer, lung cancer (such as non-small-cell lung cancer), intestinal cancer, liver cell cancer, biliary tract cancer and combination of said cancers.

Moreover, the present invention can also be applied to chronic or acute leukemia including acute myeloid leukemia, chronic myeloid leukemia, acute lymphoblastic leukemia and chronic lymphocytic leukemia, lymphocytic lymphoma, Hodgkin's disease, non-Hodgkin's lymphoma, primary CNS lymphoma and T cell lymphoma, which are categorized to so-called blood cancers.

The anti-human PD-1 antibody used in the present invention can be produced by the method described in US 2009/0217401.

The anti-human PD-1 antibody used in the present invention is generally administered systemically or locally in a parenteral form, for example, administered intravenously, intramuscularly, intradermally, intraperitoneally, or subcutaneously by injection or transfusion. Moreover, the anti-human PD-1 antibody used in the present invention may be administered with other combined drug described in, for example, US 2009/0217401.

DESCRIPTION OF EMBODIMENTS

Hereinafter, the present invention will be explained in detail by Examples, but the present invention is not limited thereto.

Example 1

Preparation of MC38 Cells for Transplantation

In the day before transplantation, $5 \times 10^6$ cells/30 mL/150 mm culture dish of MC38 cells (mouse colon adenocarcinoma (Cancer Res. (1975), 35(9), p. 2434-9)) was seeded on DMEM culture containing 10% fetal bovine serum (FBS), 100 U/mL of penicillin and 100 microgram/mL of streptomycin (hereinafter abbreviated as normal culture), and cultured for one day at 37 degrees Celsius under 5% $CO_2$/95% air.

In the day of transplantation, the culture supernatant was collected, and MC38 cells were washed with Dulbecco's phosphate buffer (D-PBS) and then collected by a normal method. The collected cells were suspended in D-PBS, and then stored on ice until just before transplantation.

Example 2

Measurement of Tumor Volume in Tumor-bearing Model of MC38 Cells

Into the right abdomen of mouse (7 weeks age, female C57BL/6NCr1Cr1j mouse (Japan Charies River Co., Ltd.); ten examples) under anesthesia, $2 \times 10^5$ cells/100 microliter/mouse of MC38 cells were subcutaneously administered. 600 microgram/200 microliter/mouse of the anti-mouse PD-1 antibody 4H2 (hereinafter, abbreviated as anti-mPD-1 antibody 4H2 or 4H2) and the mouse IgG (hereinafter abbreviated as mIgG) were intraperitoneally administered, respectively, at one hour before transplantation (day 0), and on day 3, day 6 and day 10 after transplantation.

The blood sampling from tail vein was performed the day before transplantation and on day 8 and day 15 after transplantation, and furthermore the blood was stood still for 3 hours at room temperature, and then separated into serum by centrifugation, and stored at −80 degrees Celsius. Furthermore, abdominal cavity of the mouse was opened under anesthesia on day 24 after transplantation, and the blood was drawn from the aorta abdominalis and stored, by the same method as described above.

The tumor volume ($mm^3$) was calculated by the following formula after measuring the minor axis and the major axis of the tumor by using an electronic caliper (Mitutoyo Corporation).

$$\text{Tumor Volume}(mm^3) = [(\text{Minor Axis})^2 \times (\text{Major Axis})]/2$$

FIG. 1 shows change of the tumor volumes in the control group of single administration of 600 microgram of mIgG (black square) and in the group of single administration of the same amount of anti-mPD-1 antibody (white triangle).
(Results)

As shown in FIG. 1, the anti-mPD-1 antibody 4H2 showed the effect of significantly reducing the tumor volume.

Example 3

Measurement of IgM Concentration and CD5L Concentration in the Serum

IgM concentration in serum was measured by ELISA Starter Accessory Package kit (Funakoshi Corporation) and mouse IgM ELISA Quantitation kit (Funakoshi Corporation) by following the operating procedure described in the package leaflet.

Measurement of CD5L concentration in serum was measured according to the following operating procedure. That is, 100 microliter/well of 1 microgram/mL of anti-mouse CD51, monoclonal antibody (MAB28341) in PBS dilute solution was dispensed to an ELISA plate and was stood still at 4 degrees Celsius overnight. The plate was washed three times with washing buffer (0.05% (v/v) Tween 20/PBS) (100 microliter/well), to which 100 microliter/well of blocking buffer (1% (w/v) BSA/PBS) was added, and then made to stand still at room temperature for 90 minutes.

Furthermore, the plate was washed three times with washing buffer (100 microliter/well), to which serially diluted 10 to 0.078 ng/mL, of recombinant mouse CD51, (R&D systems) and 100 microliter/well of $10^3$ times diluted serum sample were added, and then made to stand still at room temperature for 120 minutes.

The plate was washed three times with washing buffer, to which 100 microliter/well of 1 microgram/mL of anti-mouse CD5L polyclonal antibody (AF2834) was added, and then made to stand still at room temperature for 60 minutes.

Furthermore, the plate was washed three times with washing buffer, to which 100 microliter/well of $10^5$ times diluted HRP-labelled anti-goat IgG was added, and then stood still at room temperature for 60 minutes. The plate was washed three times with washing buffer, to which 100 microliter/well of TMB substrate (KPL) was added, and then stood still at room temperature for 30 minutes. 100 microliter/well of stop solution (KPL) was added to the plate, and then absorption of light at 450 nm was measured by a spectrophotometer for microplate (SPECTRAMAX™ 190; molecular device).

Figure 2:
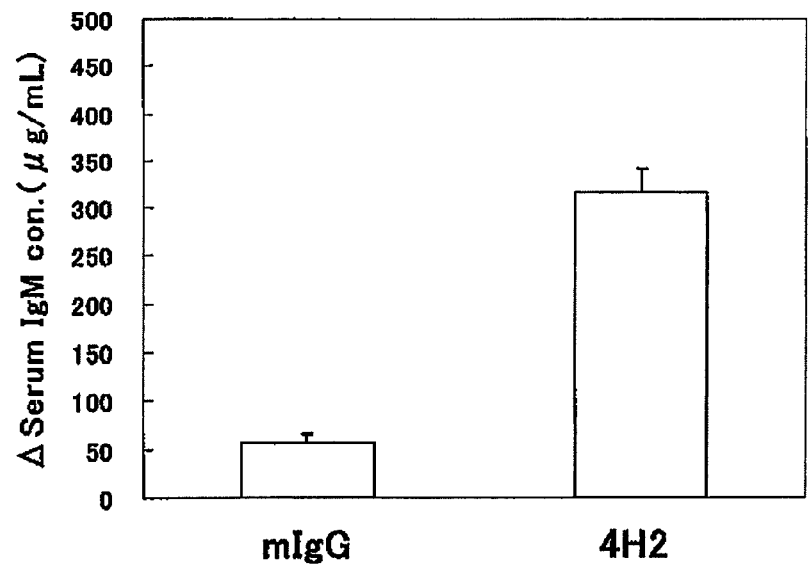
FIG. 2 shows increase of concentration of serum IgM in the administration group of the anti-mPD-1 antibody 4H2 and in the administration group of control mIgG.
Figure 3:
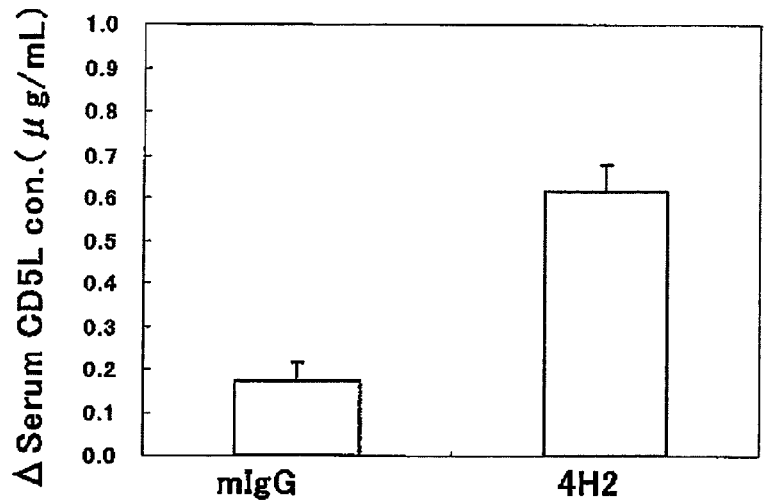
FIG. 3 shows increase of concentration of serum CD5L in the administration group of the anti-mPD-1 antibody 4H2 and in the administration group of control mIgG.

FIGS. 2 and 3 show the increase of IgM concentration in serum and CD5L concentration in serum, respectively, in the group of administration of anti-mPD-1 antibody 4H2 on day 8 after transplantation of MC38 cells and in the control group of administration of mIgG. Here, the increase of each concentration represents the increase amount from each concentration in the day before transplantation (average of ten examples for each group).

Figure 4:
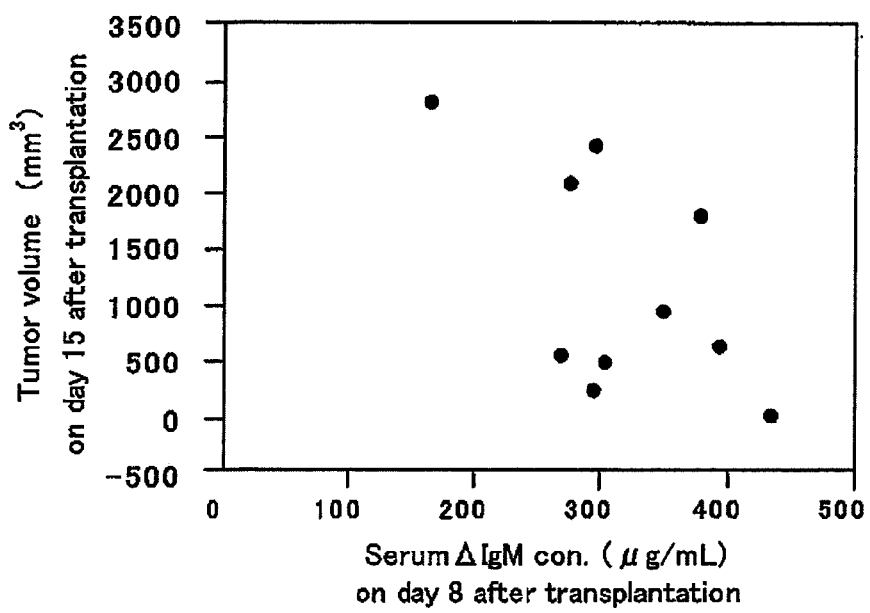
FIG. 4 shows the relationship between increase of serum IgM concentration and tumor volume of each example in the administration group of the anti-mPD-1 antibody 4H2.

FIG. 4 shows the relationship between the increase of IgM concentration in serum in the group of administration of anti-mPD-1 antibody 4H2 on day 8 after transplantation and the tumor volume on day 15 after transplantation.

(Results)

As shown in FIGS. 2 and 3, in the group of administration of anti-mPD-1 antibody 4H2, on day 8 after transplantation in which the effect to the tumor volume could not be confirmed, the increase of IgM concentration in serum and the increase of CD5L concentration in serum were more significant than that of the group of administration of control mIgG ($P<0.05$; Student's t-test). Moreover, as shown in FIG. 4, it was recognized that the increase of IgM concentration in serum in the group of administration anti-mPD-1 antibody 4H2 has an inverse relation (correlation coefficient: −0.58) with the tumor volume thereof. Similarly, CD5L also showed an inverse relation.

Example 4

39 patients with recurrent or treatment-refractory solid tumors (including non-small cell lung cancer, renal, colon, melanoma and hormone-refractory prostate cancer) received single dose treatment of 0.3, 1, 3 or 10 mg/kg of the human anti-PD-1 antibody. The sera from patients were collected at 1 day before first dosing, and 29 days, 57 days and 85 days after first dosing. These sera were frozen until measurement of biomarker concentration. After thawing these sera, the concentration of the immunoglobulins (including IgM, IgA, $IgG_1$, $IgG_2$, $IgG_3$ and $IgG_4$) were measured.

(Result)

Figure 5:
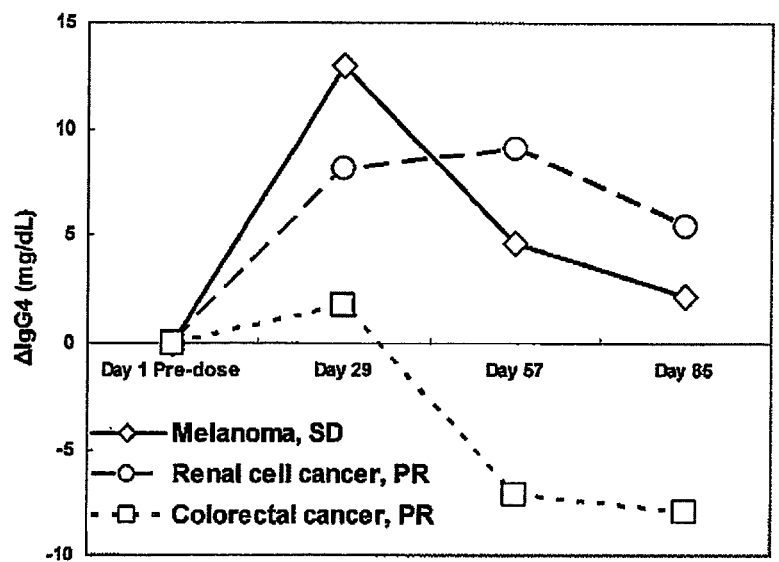
FIG. 5 shows increase of concentration of serum $IgG_4$ in cancer patients who experienced a confirmed partial response or a stable disease by administration of the human anti-human PD-1 antibody.

Disease status was evaluated by RECIST criteria. Anti tumor activity were observed, including two patients with colorectal cancer (received the treatments of the anti-human PD-1 antibody of 3 mg/kg) and renal cell cancer (received the treatments of the anti-human PD-1 antibody of 10 mg/kg), who experienced a confirmed partial response, and one patient with melanoma (received the treatments of the anti-human PD-1 antibody of 10 mg/kg), who experienced a stable disease. As shown in the FIG. 5, the concentrations of $IgG_4$ after administering the initial dose of the anti-human PD-1 antibody are higher than those prior to administering the initial dose.

INDUSTRIAL APPLICABILITY

The anti-human PD-1 antibody used in the present invention can be continuously administered to the patient in whom its effect can be expected in future, and is useful as a new prescription of the anti-human PD-1 antibody as an active ingredient. Moreover, the method for estimating or optimizing the therapeutic efficacy of the anti-human PD-1 antibody used in the present invention on cancer is useful as means for providing the anti-human PD-1 antibody used in the present invention to the cancer patient in whom its effect can be expected.

The invention claimed is:

1. A method for evaluating the therapeutic efficacy of an anti-human PD-1 antibody in treating a cancer, comprising:
   (a) determining the pre-administration concentration(s) of one or more efficacy markers in the cancer patient's blood, wherein the one or more efficacy markers is/are selected from the group consisting of immunoglobulin(s), CD5 antigen-like protein, gelsolin, and fragments thereof;
   (b) administering an initial dose or doses of the anti-human PD-1 antibody to the cancer patient and determining the post-administration concentration(s) of said efficacy marker(s) in the patient's blood;
   (c) comparing the post-administration concentration(s) of said efficacy marker(s) with their pre-administration concentration(s); and
   (d) evaluating whether the anti-human PD-1 antibody is effective in treating the cancer, wherein at least a three-fold increase in the post-administration concentration(s) of the one or more efficacy markers compared to the pre-administration concentration(s) indicates that the anti-human PD-1 antibody is efficacious in treating the cancer.

2. The method of claim 1, wherein the post-administration concentration(s) of step (c) is/are determined before the twelfth week after administering the initial dose.

3. The method of claim 1, wherein the post-administration concentration(s) of step (c) is/are determined before the eighth week after administering the initial dose.

4. The method of claim 1, wherein the immunoglobulin(s) is/are one or more isotypes selected from the group consisting of IgM, IgG and IgA.

5. The method of claim 4, wherein IgG is IgG4.

6. The method of claim 1, wherein the anti-human PD-1 antibody is a human anti-human PD-1 antibody.

7. The method of claim 6, wherein the human anti-human PD-1 antibody is selected from the group consisting of:
   a) an antibody comprising a $V_H$ region comprising amino acids having the sequence set forth in SEQ ID NO: 1; and a $V_L$ region comprising amino acids having the sequence set forth in SEQ ID NO: 8;
   b) an antibody comprising a $V_H$ region comprising amino acids having the sequence set forth in SEQ ID NO: 2; and a $V_L$ region comprising amino acids having the sequence set forth in SEQ ID NO: 9;
   c) an antibody comprising a $V_H$ region comprising amino acids having the sequence set forth in SEQ ID NO: 3; and a $V_L$ region comprising amino acids having the sequence set forth in SEQ ID NO: 10;
   d) an antibody comprising a $V_H$ region comprising amino acids having the sequence set forth in SEQ ID NO: 4; and a $V_L$ region comprising amino acids having the sequence set forth in SEQ ID NO: 11;
   e) an antibody comprising a $V_H$ region comprising amino acids having the sequence set forth in SEQ ID NO: 5; and a $V_L$ region comprising amino acids having the sequence set forth in SEQ ID NO: 12;
   f) an antibody comprising a $V_H$ region comprising amino acids having the sequence set forth in SEQ ID NO: 6; and a $V_L$ region comprising amino acids having the sequence set forth in SEQ ID NO: 13; and
   g) an antibody comprising a $V_H$ region comprising amino acids having the sequence set forth in SEQ ID NO: 7 and a $V_L$ region comprising amino acids having the sequence set forth in SEQ ID NO: 14.

8. The method of claim 1, wherein the cancer patient is a patient having one or more kinds of solid cancers.

9. The method of claim 8, wherein one or more kinds of solid cancers is/are selected from the group consisting of malignant melanoma, kidney cancer, prostate cancer, breast cancer, lung cancer, pancreatic cancer, intestinal cancer, liver cell cancer, biliary tract cancer, stomach cancer, ovary cancer, esophageal cancer, and urothelial cancer.

10. A method of optimizing the therapeutic efficacy of an anti-PD-1 antibody in treating a cancer comprising evaluating the therapeutic efficacy of the antibody by the method of claim 1, and adjusting the dosage of the antibody based on the evaluated therapeutic efficacy.

11. A method of treating a cancer patient with an anti-PD-1 antibody comprising evaluating the therapeutic efficacy of the antibody by the method of claim 1, and further administering the antibody to the patient based on the evaluated therapeutic efficacy.

12. A method of identifying a cancer patient as a suitable candidate for treatment with an anti-PD-1 antibody comprising evaluating the therapeutic efficacy of the antibody in the patient by the method of claim 1, and identifying the patient as a suitable candidate if the antibody is determined to be efficacious in the patient.

13. The method of claim 10, wherein the post-administration concentration(s) of step (c) in the method of claim 1 is/are determined before the eighth week after administering the initial dose.

14. The method of claim 10, wherein the cancer is one of more kinds of solid cancers.

15. The method of claim 14, wherein one or more kinds of solid cancers is/are selected from the group consisting of malignant melanoma, kidney cancer, prostate cancer, breast cancer, lung cancer, pancreatic cancer, intestinal cancer, live cell cancer, biliary tract cancer, stomach cancer, ovary cancer, esophageal cancer, and urothelial cancer.

16. The method of claim 12, wherein the post-administration concentration(s) of step (c) in the method of claim 1 is/are determined before the eighth week after administering the initial dose.

17. The method of claim 12, wherein the cancer patient is a patient having one or more kinds of solid cancers.

18. The method of claim 17, wherein one or more kinds of solid cancers is/are selected from the group consisting of malignant melanoma, kidney cancer, prostate cancer, breast cancer, lung cancer, pancreatic cancer, intestinal cancer, liver cell cancer, biliary tract cancer, stomach cancer, ovary, cancer, esophageal cancer, and urothelial cancer.

* * * * *